United States Patent
Kettwig et al.

(10) Patent No.: US 8,906,112 B2
(45) Date of Patent: Dec. 9, 2014

(54) PROSTHESIS SOCKET AND SYSTEM COMPRISING A PROSTHESIS SOCKET AND PROSTHESIS DEVICE

(75) Inventors: Thomas Kettwig, Luedersdorf (DE); Bernard Garus, Einbeck (DE); Sven Zarling, Duderstadt (DE); Felix Ruess, Gerasdorf (DE)

(73) Assignee: Otto Bock HealthCare GmbH, Duderstadt (DE)

( * ) Notice: Subject to any disclaimer, the term of this patent is extended or adjusted under 35 U.S.C. 154(b) by 370 days.

(21) Appl. No.: 12/670,458

(22) PCT Filed: Jul. 25, 2008

(86) PCT No.: PCT/DE2008/001243
§ 371 (c)(1),
(2), (4) Date: Jan. 25, 2010

(87) PCT Pub. No.: WO2009/012774
PCT Pub. Date: Jan. 29, 2009

(65) Prior Publication Data
US 2010/0191348 A1      Jul. 29, 2010

(30) Foreign Application Priority Data
Jul. 26, 2007   (DE) .......................... 10 2007 035 410

(51) Int. Cl.
*A61F 2/72*    (2006.01)
*A61F 2/80*    (2006.01)
*A61F 2/78*    (2006.01)
*A61F 2/30*    (2006.01)

(52) U.S. Cl.
CPC ........... *A61F 2/80* (2013.01); *A61F 2250/0021* (2013.01); *A61F 2002/7862* (2013.01); *A61F 2002/30024* (2013.01); *A61F 2002/7881* (2013.01); *A61F 2/78* (2013.01); *A61F 2250/0018* (2013.01); *A61F 2002/7893* (2013.01)
USPC .................................. 623/27; 623/33; 623/38

(58) Field of Classification Search
USPC ...................................................... 623/33, 38
See application file for complete search history.

(56) References Cited

U.S. PATENT DOCUMENTS 4,161,042 A * 7/1979 Cottingham et al. ........... 623/33
4,872,879 A   10/1989 Shamp
(Continued)

FOREIGN PATENT DOCUMENTS

DE     3229812       8/1982
EP     1656911       11/2004
(Continued)

*Primary Examiner* — Bruce E Snow
*Assistant Examiner* — Melissa Hoban
(74) *Attorney, Agent, or Firm* — Whitman Curtis Christofferson & Cook, PC (57) ABSTRACT

A prosthesis socket for receiving an amputation stump has at least one shell which has an arched, open cross-section, where the shell ends in the applied state overlap each other at least partially. At least one tensioning means is disposed on the shell to act in a circumferential direction for tensioning the shell ends relative to each other. The shell is being made of a dimensionally stable plastic having regions with varying elasticity. The proximal end of the socket is relatively more flexible. The inner surface of the socket includes a direction dependent surface to aid in holding the amputation stump. A connector for the distal prosthesis is preferentially positioned adjacent the patient's greater trochanter and is configured for pivotable bearing of the prosthesis with fixing devices to secure the orientation of the prosthesis relative to the socket.

29 Claims, 8 Drawing Sheets

(56) References Cited

U.S. PATENT DOCUMENTS

| | | | |
|---|---|---|---|
| 5,529,575 A | 6/1996 | Klotz | |
| 5,571,209 A | 11/1996 | Brown, Sr. | |
| 5,651,792 A * | 7/1997 | Telikicherla | 623/36 |
| 5,653,766 A | 8/1997 | Naser | |
| 5,728,165 A | 3/1998 | Brown, Sr. | |
| 6,077,300 A * | 6/2000 | Sabolich et al. | 623/37 |
| 7,300,466 B1 * | 11/2007 | Martin | 623/31 |
| 2004/0143345 A1 * | 7/2004 | Caspers | 623/36 |
| 2004/0158332 A1 * | 8/2004 | Carstens | 623/27 |
| 2004/0236434 A1 * | 11/2004 | Carstens | 623/34 |
| 2006/0009860 A1 * | 1/2006 | Price, Jr. | 623/33 |
| 2006/0111792 A1 * | 5/2006 | Shannon | 623/36 |
| 2006/0173553 A1 * | 8/2006 | Holzer et al. | 623/32 |
| 2007/0185425 A1 * | 8/2007 | Einarsson et al. | 602/26 |
| 2007/0264482 A1 * | 11/2007 | Banker et al. | 428/223 |
| 2010/0036505 A1 | 2/2010 | Hassler | |

FOREIGN PATENT DOCUMENTS

| | | |
|---|---|---|
| FR | 2512666 | 3/1983 |
| GB | 675811 | 4/1950 |
| GB | 702696 | 9/1952 |
| GB | 2103490 A | 2/1983 |
| JP | 57-187513 | 11/1982 |
| JP | 2002291781 A | 10/2002 |
| JP | 2003-299679 | 10/2003 |
| JP | 2005034257 A | 2/2005 |
| SU | 1261649 A1 | 10/1986 |
| SU | 1208326 A1 | 5/1987 |
| UA | 59759 C2 | 9/2003 |
| WO | 2006/066951 A2 | 6/2006 |

* cited by examiner

PROSTHESIS SOCKET AND SYSTEM COMPRISING A PROSTHESIS SOCKET AND PROSTHESIS DEVICE

FIELD OF THE INVENTION

The invention relates to a prosthesis socket for receiving an amputation stump of an extremity, with connecting means for a distal prosthesis device, and a system comprising a prosthesis socket and a prosthesis device.

BACKGROUND

The prior art discloses various methods and concepts by which patients who have undergone amputations, e.g., of the lower extremities, are fitted with a prosthesis. In patients whose legs have been amputated above or below the knee or through the knee joint, a classical method for producing a prosthesis socket is the plaster east method, in which a plaster cast is made of a patient's amputation stump and serves as a template for a stump model, and a prosthesis socket, for example a thigh socket, is formed on this stump model. This thigh socket is made from a plastic and completely surrounds the amputation stump.

Various concepts have been proposed for securing the thigh socket to the stump. For example, a liner is pulled over the amputation stump and bears sealingly on the outside on the socket. The air is removed from the space between the liner and the outer socket by way of a release valve or a pump, such that the prosthesis socket is held on the amputation stump of the patient by means of underpressure. In the case of a release valve, the air taken is released at each step, and active evacuation does not take place. In the case or a pin solution, the end of the liner is provided with a projection that is locked in the socket. Further prosthesis devices are then, arranged an the prosthesis socket itself, for example prosthetic knee joints and additional devices such as a connecting element and prosthetic foot.

Adapting a prosthesis socket individually to the amputation stump is extremely difficult and time-consuming and has to be done by a trained orthopedic technician. Several fittings are needed in order to individually adapt the prosthesis socket, with the result that nine to twelve months may pass between the operation and the final provision of an adapted prosthesis socket. These prosthesis sockets ensure a high degree of stability and activity of the prosthesis user. Patients with an amputation of an upper extremity are treated in a comparable manner.

However, the patients who are to be provided with prosthesis devices do not all have the same requirement for extensive mobility. For example, elderly subjects who are suffering from diabetes, and who have had to have parts of the lower extremities amputated on account of gangrene induced by diabetes, are often enable so walk long distances. In addition, there are considerable fluctuations in the volume of the amputation stump, such that a correct adaptation of the prosthesis socket to the stump is possible only with difficulty. Moreover, the patient is often unable to cooperate actively in the adaptation of the prosthesis socket. However, it is particularly important for these very patients to be fitted with a prosthesis as soon as possible in order to be able to minimize the period of confinement to bed. When treating the upper extremities, it is also important to adept a prosthesis as quickly as possible in order to ensure that motor capacity is not lost.

EP 1 656 911 A1 describes a prosthesis socket with a closed shell and with an element which is arranged laterally therein and which is pulled in the direction of the stump via a tensioning strap that is guided into the shell through two slits. The bottom of the shell is padded and has connecting means for a lower leg.

DE 32 29 812 A1 relates to a stump-receiving shell for an artificial limb, with at least one shell which has a curved, open cross section and of which the ends at least partially overlap each other in the state when applied. Tensioning means arranged on the shell act in the circumferential direction and clamp the shell ends on each other.

SUMMARY

The object of the present invention is to make available, particularly for geriatric patients, a prosthesis socket and a system composed of a prosthesis socket and of prosthesis devices secured thereon, permitting rapid adaptation to the patient and inexpensive fitting, such that the patient remains active or is mobile again as soon as possible.

In the prosthesis socket according to the invention for receiving an amputation stamp of an extremity, with connecting means for a distal prosthesis device, the prosthesis socket comprises at least one shell, which has a curved, open cross section and of which the shell ends, in the applied state, at least partially overlap each other, and at least one tensioning means is arranged on the shell and is active in the circumferential direction. The tensioning means permits rapid and easy adaptation of the prosthesis socket, in particular the thigh socket, to the contour of the amputation stump, since the tensioning can bring about a radial shifting of the shell ends toward each other, with the result that it is no longer necessary to take individual impressions. By provision of the tensioning means, the prosthesis socket, and therefore the entire prosthesis, can also be applied and taken off again quickly and easily, thereby increasing the acceptance of the prosthesis by the prosthesis user. In this way, patients who have only recently undergone surgery can be quickly fitted with a prosthesis, with the result that the period of reduced mobility or activity is reduced. The shell can be spiral-shaped, for example, allowing the circumference of the socket to be modified via the one pr more tensioning means. Likewise, two mutually opposite shell areas can overlap each other such that, when the effective length of the one or more tensioning means is changed, a folding overlapping movement takes place instead of a rotating overlapping movement. The shell can be configured in one piece. The shell or partial shells are preferably produced from, a dimensionally stable plastic in order to allow the prosthesis socket to be made as light as possible. The shell or partial shells have areas of different elasticity in order, on the one hand, to satisfy the stability requirements and, on the other hand, to ensure comfort during use. Thus, the shell or partial shells are made flexible in the proximal area for example, particularly in the frontal and dorsal directions, such that the patient does not find it uncomfortable to be sitting down with the prosthesis applied. The areas of different flexibility can be obtained by using materials having different physical properties or by using different thicknesses of material. The more flexible areas are generally thinner than the stiffer areas or can be made from a more flexible material than the rest of the shell, for example by two-component injection molding.

The shell can be made up of several partial shells, which are designed to be able to move relative to one another. Two or more partial shells can be combined to make one overall shell in which the partial shells are arranged like leaves at least partially overlapping each other. The partial shells can also be connected to one another or formed integrally on one another in their distal areas, such that, an elastic bearing for several shell-like parts is formed at one common area.

The shell or partial shells are preferably arranged medially and laterally on the amputation stump and each have at least one connecting means for the distally adjoining prosthesis device. The medial/lateral arrangement makes it possible for the overlapping of the shell ends or partial shells to be arranged at the front and rear, in order to achieve increased stability there. With this arrangement, the connecting means for securing the prosthesis, device can also, be provided medially and laterally. In an alternative embodiment, there is a unilateral attachment permitting either a medial or lateral arrangement of the connecting means, thereby increasing the range of configurations of the prosthesis. In this way, individual preferences or needs can be more easily taken into consideration.

The shell or partial shells are medially and laterally stiff and have a high degree of resistance to deformation, particularly against bending about an axis in the forward direction, or direction of walking, so as to be able to provide sufficient stability. The stiffness is supported by a curvature of the shell or partial, shells. The shell or shells can also be attached to the frame on one side. This unilateral attachment can either be on the medial or lateral side.

Easier adaptation and overlapping of the shell or partial shells is permitted by providing them with a curvature, such that they can be pushed or plugged into each other. In this case, one partial shell has a greater radius of curvature than the other partial shell, such that one partial shell can be overlapped oh the outside by the other at both ends. It is also possible to perform an approximate preliminary shaping to the form of the stump.

The connecting means for securing the distal prosthesis device are preferably arranged in the proximal, stiff area of the shell or partial shells. Particularly in the case of above-knee amputations, the connecting means are positioned in the area of the greater trochanter. In a development of the invention, the center of rotation of the connecting means is arranged in the area of the greater trochanter, while the connecting means themselves are secured on another part of the shell or of the partial shells. For example, the rotation point can be moved in the direction of the greater trochanter via suitably curved guides.

The connecting means can be arranged or designed for the pivotable bearing of the prosthesis device, the pivotability being provided only for a small angle range in order to facilitate the prosthesis setup, that is to say the orientation of the prosthesis elements with respect to one another and to the body. After the prosthesis setup has been finalized, the prosthesis device can be fixed in the correct position via fixing devices, for example screws or pins. The fixing device can be guided in an oblong hole, for example in a curved oblong hole, in order to facilitate the prosthesis setup.

In principle, the shell or partial shells, in the applied state or when connected to each other, form an opening both at the proximal end and also at the distal end. In order to close this opening, a cap is secured, in particular releasably secured, as a distal closure piece on the shell or at least a partial shell, in order to protect the distal end of the amputation stump.

In order to facilitate the insertion of the amputation stump provided with a liner and also to ensure a stable relationship between amputation stump and prosthesis socket, the inner face of the shell or partial shells is provided or coated with a direction-dependent surface configuration, e.g. a nap velour, which has an orientation permitting easy insertion hut offering increased resistance counter to the direction of insertion. The surface configurations, e.g. fibers, are for this purpose inclined in the distal direction, while the outer face of the liner has a configuration or coating in an oppositely directed nap or is provided with a surface suitably interacting with the surface configuration, or the velour. The design of the socket and of the liner with direction-dependent surface configurations can also be used independently of the construction of the socket in other designs of the socket and represents an independent solution to the problem of holding a liner in a socket.

Alternatively or in addition to this, the inner face of the partial shells is coated with an adhesive layer, for example of silicone, polyurethane or a copolymer, or if appropriate provided only in some areas with an adhesive coating, in order to ensure better adherence to a liner that is provided with a corresponding outer coating.

The tensioning means provided can be velcro tapes, ski-boot fasteners, clips or straps, and alternative securing means can also be provided for the variable adjustment of the circumference of the shell or of the spacings or overlaps of the partial shells and for securing the partial shells or the ends of the shells to each other. The tensioning means are preferably arranged and guided on the outer face of the socket, in order to avoid direct contact with the stump and thus avoid the danger of the stump becoming caught.

The tensioning means can be guided across the front. In particular, the closure devices or levers are arranged at the front in order to make the prosthesis and the prosthesis socket easy to apply and to take off. The one or more tensioning means preferably act in a circular configuration.

For individual adaptation of the shell or partial shells to the stump contour, at least two tensioning means are axially offset relative to each other on the prosthesis socket, as a result of which a cone is formed that widens in the proximal direction. The fluctuations in volume, which can differ in degree along the length of the amputation stump, can also be better compensated for when several tensioning means are used. The tensioning means can also be arranged with two axially offset guides.

The prosthesis device to be secured on the prosthesis socket comprises a frame which is secured preferably laterally and/or medially on the prosthesis socket, the frame preferably being designed as an outer frame, which is produced from a metal profile, for example. Securing on one side may be sufficient, in which case medial securing is preferably chosen. The further prosthesis devices, for example a prosthetic knee joint or the like, can then be secured on the frame. The prosthesis socket and the prosthesis device, which can in each case be differently designed depending on the height of the amputation, form a system for fitting a patient with a prosthesis.

DESCRIPTION OF THE DRAWINGS

Illustrative embodiments of the invention are explained in more detail below with reference to the attached figures, in which.

DESCRIPTION

Figure 1:
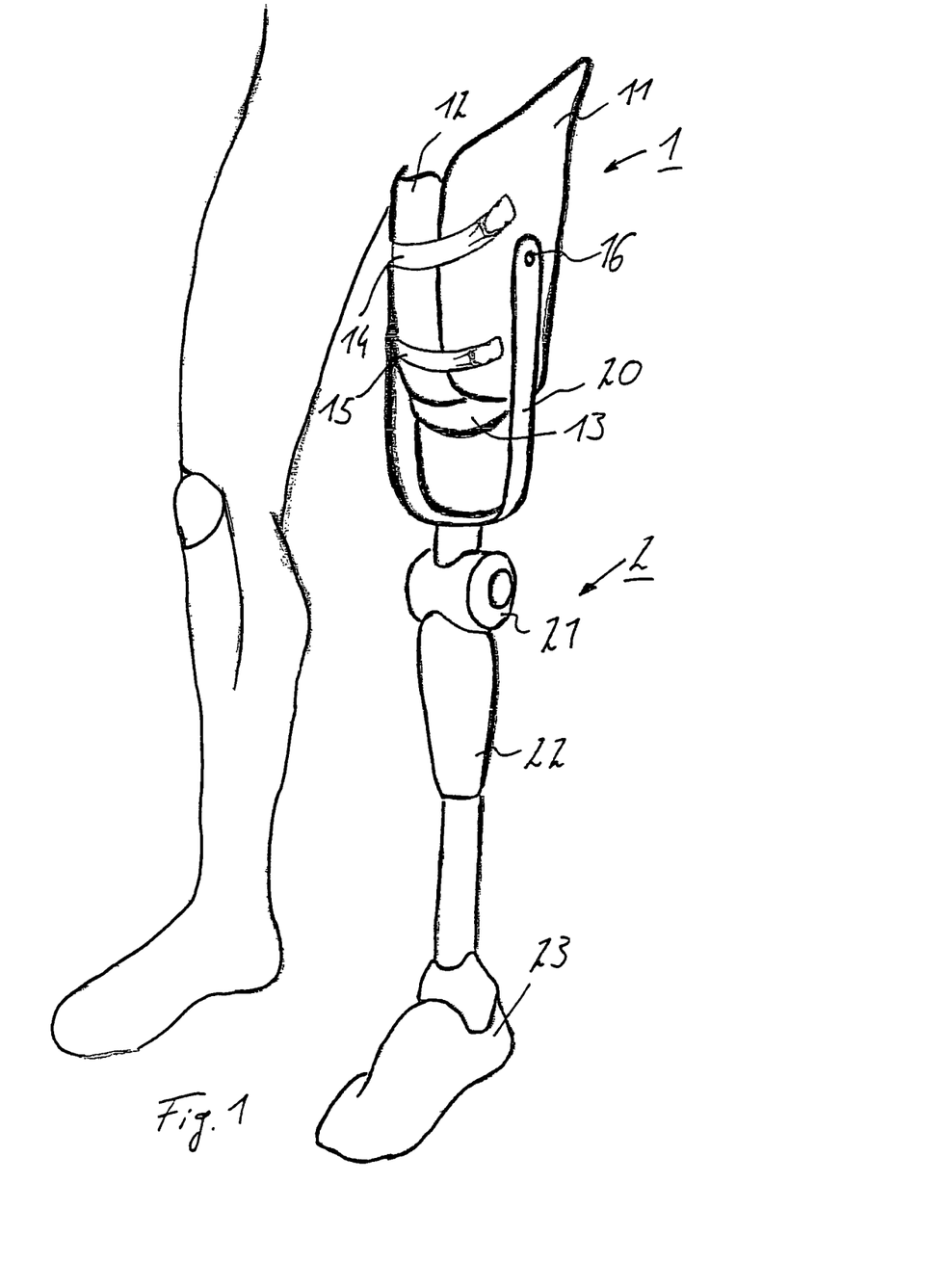
FIG. 1 shows a system comprising prosthesis socket and prosthesis device, in the state when applied.

In FIG. 1, a system comprising a prosthesis socket 1, here a thigh socket, and a prosthesis device 2 secured thereon is shown in a state when applied, along with a schematic depiction of the healthy right leg. In this illustrative embodiment, the prosthesis socket 1 is composed of two partial shells 11, 12 which are arranged around the amputation stump and overlap each other. The prosthesis socket 1 is adapted to the circumference and the contour of the amputation stump via two tensioning means 14, 15 that are secured and axially offset from each other on the partial shells 11, 12. Arranged between the prosthesis socket 1 and the amputation stump there is a liner (not shown), which is pulled over the amputation stump and completely avoids direct contact of the partial shells 11, 12 with the skin, of the amputation stump. A mechanical coupling between the prosthesis socket 1 and the amputation stump is produced by the liner.

The two partial shells 11, 12 are produced from a planar, dimensionally stable plastic and have a curvature, such that they bear with the greatest possible surface area on the prosthesis socket or the liner. In the embodiment shown, the medial partial, shell 12 is overlapped on the outside by the lateral partial shell 11 in the frontal area. A corresponding overlap can also take place in the dorsal area, which means that the radius of curvature of the lateral partial shell 11 is greater than that of the medial partial shell 12. The separate partial shells 11, 12 have an open cross section and, in the applied state, form a multi-part sleeve that is open at the proximal and distal ends. The distal end of the prosthesis socket 1 is here closed by a cap 13, which is secured on the partial shells 11, 12. The cap 13 serves to protect the distal end of the amputation stump. In principle, it is also possible for this cap 13 to be secured or formed on the liner.

In the proximal area of the prosthesis socket 1, the partial shells 11, 12 are provided with connecting means 16 for securing a frame 20. Although the connecting means 16, which are designed as a screw connection, are shown only on the lateral side, they are in fact present on both partial, shells 11, 12. The frame 20 is formed as a U-shaped bracket from a metal or plastic profile and serves as an enter frame, in order to place the least possible strain on the prosthesis wearer. The two arms of the U-shaped outer frame 20 are arranged medially and laterally.

The frame 20 is adjoined distally by further components of the prosthesis device 20, in this case a prosthetic knee joint 21, a connection element 22 and a prosthetic foot 23. The prosthesis device 2 as a whole is preferably designed as a lockable knee joint or a high-stability knee joint, which has a simple construction and above all avoids any undesired bending-in of the prosthetic knee joint 21. Where the system is not used for the management of geriatric patients, but instead as a form of primary treatment, other constructions of the prosthetic knee joint 21 can also be provided.

Figure 2:
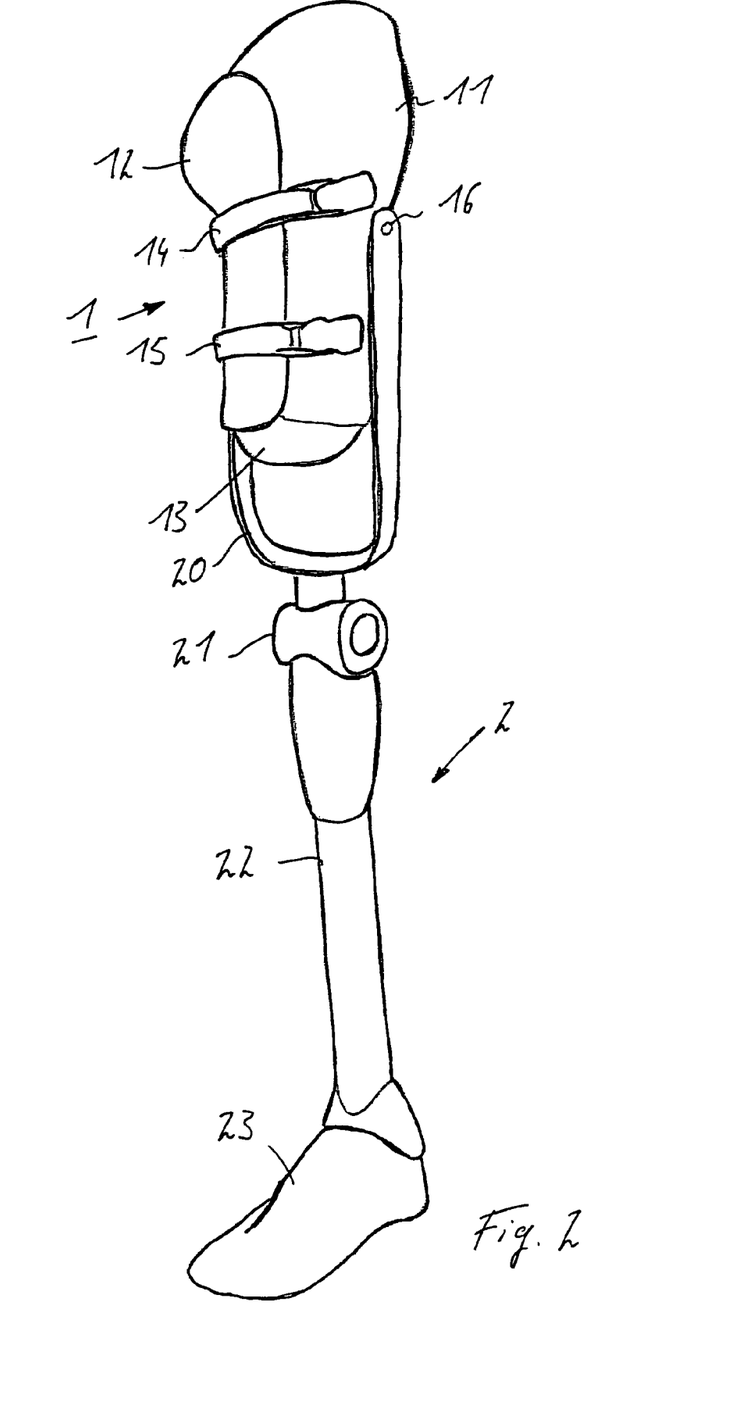
FIG. 2 shows a separate view of the prosthesis socket and of a prosthesis device secured thereon.

The system comprising prosthesis socket 1 and prosthesis device 2 is shown separately in FIG. 2. In contrast to FIG. 1, the medial partial shell 12 is here arranged on the outside and overlaps the lateral partial shell 11. The tensioning means 14, 15, which can be designed as straps, velcro tapes or, for example, ski-boot fasteners, can either be secured on just one partial shell 11, 12 and act in the circumferential direction, such that the partial shells 11, 12 are moved toward each other, or they can establish the connection between the two partial shells 11, 12, such that one end point of a tensioning means 14, 15 is arranged on the medial partial shell 12 and a second end point is arranged on the lateral partial shell 11.

Since the system comprising prosthesis socket 1 and prosthesis device 2 appears particularly suitable for less active patients who are frequently seated, pressure sores can be avoided, and comfort enhanced, if the prosthesis socket 1 is soft and flexible in the frontal and dorsal areas, particularly in the proximal area the partial shells 11, 12, while the distal area of the partial shells 11, 12 is stable, particularly on the medial and lateral sides. The area of the connecting means 16 in particular is stable, such that the forces that occur during walking or standing can be introduced into the prosthesis socket 1. The connecting means 16 are secured as far as possible in the proximal direction on the partial shells 11, 12, preferably in the area of the greater trochanter when the prosthesis socket 1 is designed as a thigh socket.

Figure 3:
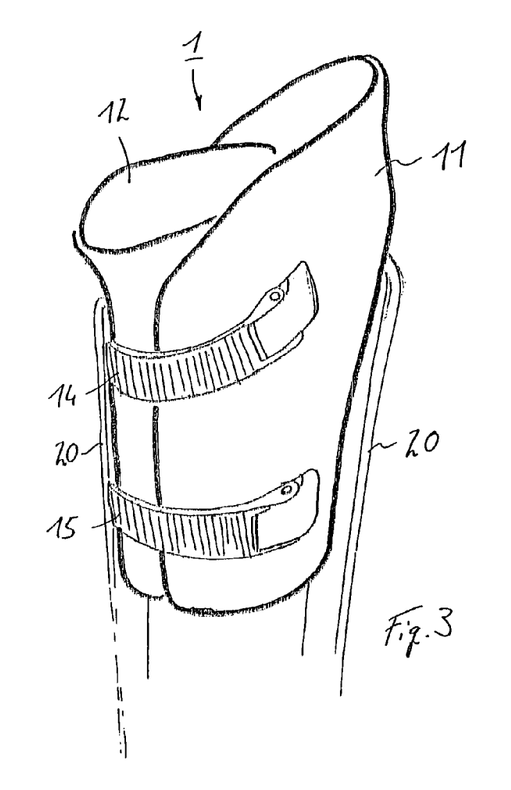
FIG. 3 shows a detail of an assembled prosthesis socket.

FIG. 3 shows an enlarged detail of the prosthesis socket 1 with the two partial shells 11, 12 and the tensioning means 14, 15 which, via interlocking devices, are designed to adjust the circumference of the prosthesis socket 1. The preshaped partial shells 11, 12 have a sufficient degree of flexibility, and at the same time stability, to provide sufficiently exact adaptation to the amputation stump when the tightness of the tensioning means 14, 15 is altered. The outer frame 20 with the brackets is secured medially and laterally, in particular for a screw connection.

Figure 4:
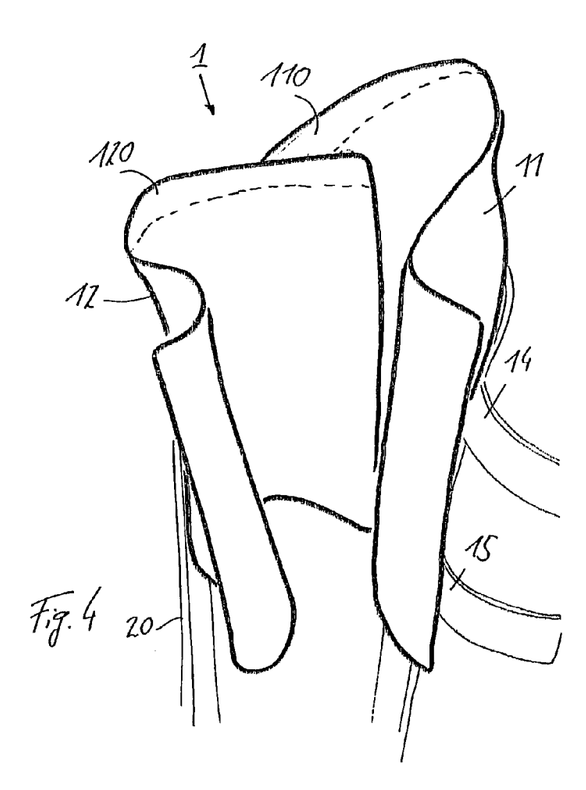
FIG. 4 shows a prosthesis socket with separate partial shells.

FIG. 4 shows the prosthesis socket 1 when opened, it will be noted that the medial partial shell 12 is received in the lateral partial shell 11 and is overlapped by the latter to the front and back. In the proximal areas 110, 120 of the partial shells 11, 12, zones of lesser strength and increased flexibility are formed, which make sitting easier. The wall thickness in these areas 110, 120 can also be reduced in order to make sitting easier when the prosthesis is applied. The tensioning means 14, 15 are shown in the opened state. By opening up the tensioning means 14, 15, it is possible to open the prosthesis socket 1 such that the prosthesis wearer can very easily apply the prosthesis socket 1 by climbing into the opened prosthesis socket 1, pushing the partial shells 11, 12 into each other and, when necessary, closing the tensioning means 14, 15. By virtue of the variable configuration of the tensioning means 14, 15, it is possible to take account of changes in the volume of the amputation stump and at all times to ensure a sufficiently secure fastening of the prosthesis socket 1 to the amputation stump, particularly to the liner.

Figure 5:
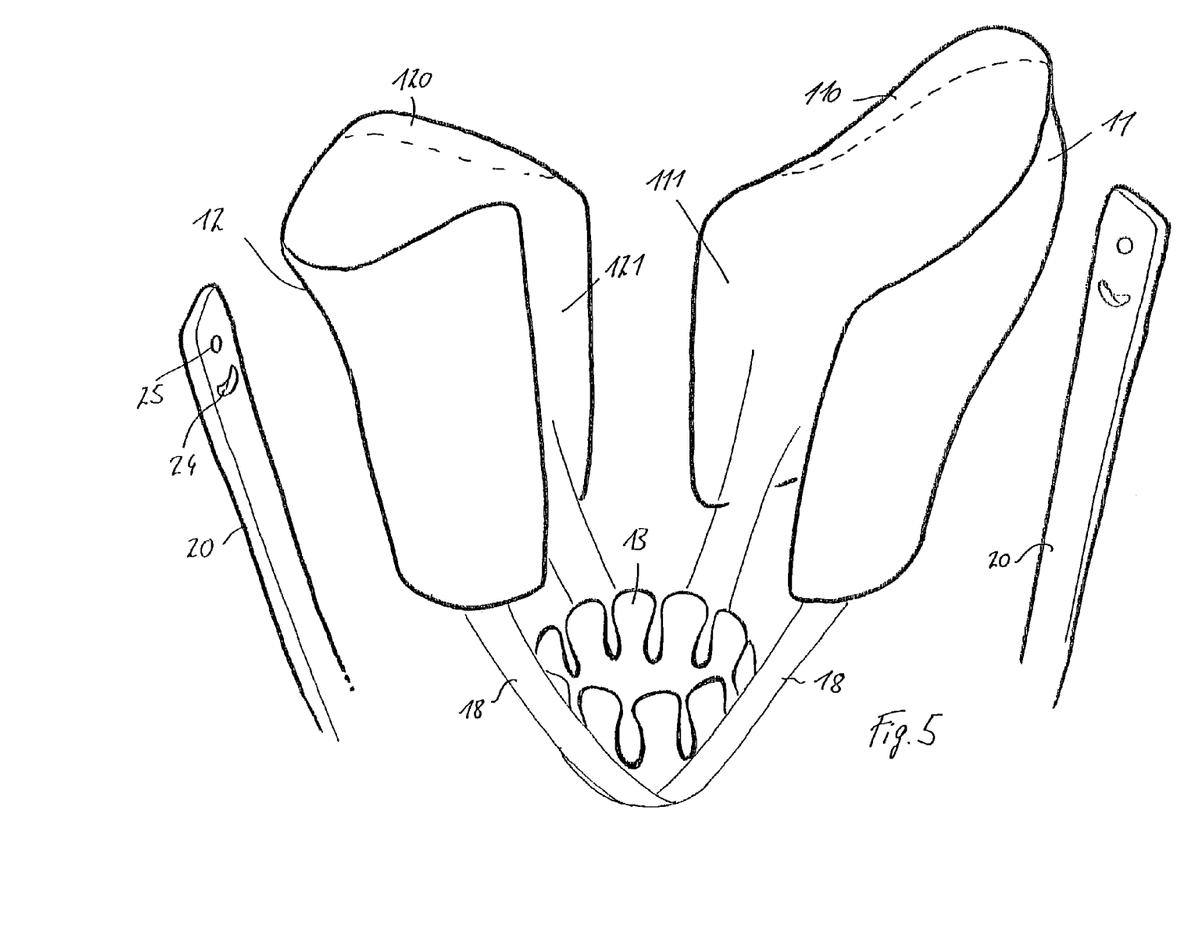
FIG. 5 shows a prosthesis socket in an exploded view.

FIG. 5 shows the prosthesis socket 1 in an exploded view. The lateral partial shell 11 is designed such that it covers the greater trochanter, while the medial partial shell 12 is designed such that the ischium is not covered or only comes into contact with the flexible area 120. The cap 13 is secured to the distal ends of the partial shells 11, 12 via securing tapes 18, for example velcro tapes. The securing tapes 18 are arranged crosswise and hold the cap 13 on the prosthesis socket 1, the open edge of the cap 13 forming elastic fingers.

The inner faces 111, 121 of the partial shells 11, 12 can be provided with various coatings in order to permit adherence to the liner or coupling between liner and partial shells, 11, 12. The coating 111, 121 can be designed, for example, as a nap velour or as another fabric with a suitable orientation of the fibers, making it easier to insert the liner and the amputation stump into the substantially tube-shaped prosthesis socket 1 and at the same time preventing them from slipping out. For this purpose, the fibers or hooks can be inclined in the direction of the distal edge, such that a movement of insertion is made easier, whereas a movement in the apposite direction, is blocked or made difficult. To release the socket 1 from the liner, the tensioning means 14, 15 are opened up, and the prosthesis socket 1 is removed together with the prosthesis device 2. It is also possible to coat the inner face of the partial shells 11, 12 with a copolymer or silicone in order to support the adherence of the liner, which is provided on the outside with a corresponding coating.

FIG. 5 also shows the outer frame 20, of which the proximal end has bores 25 through which the connecting means 16 in the form of screws or pins are guided. Curved oblong holes 24 are also formed in the frame 20 and receive means for fixing the prosthesis socket 1 relative to the frame 20.

Figure 6:
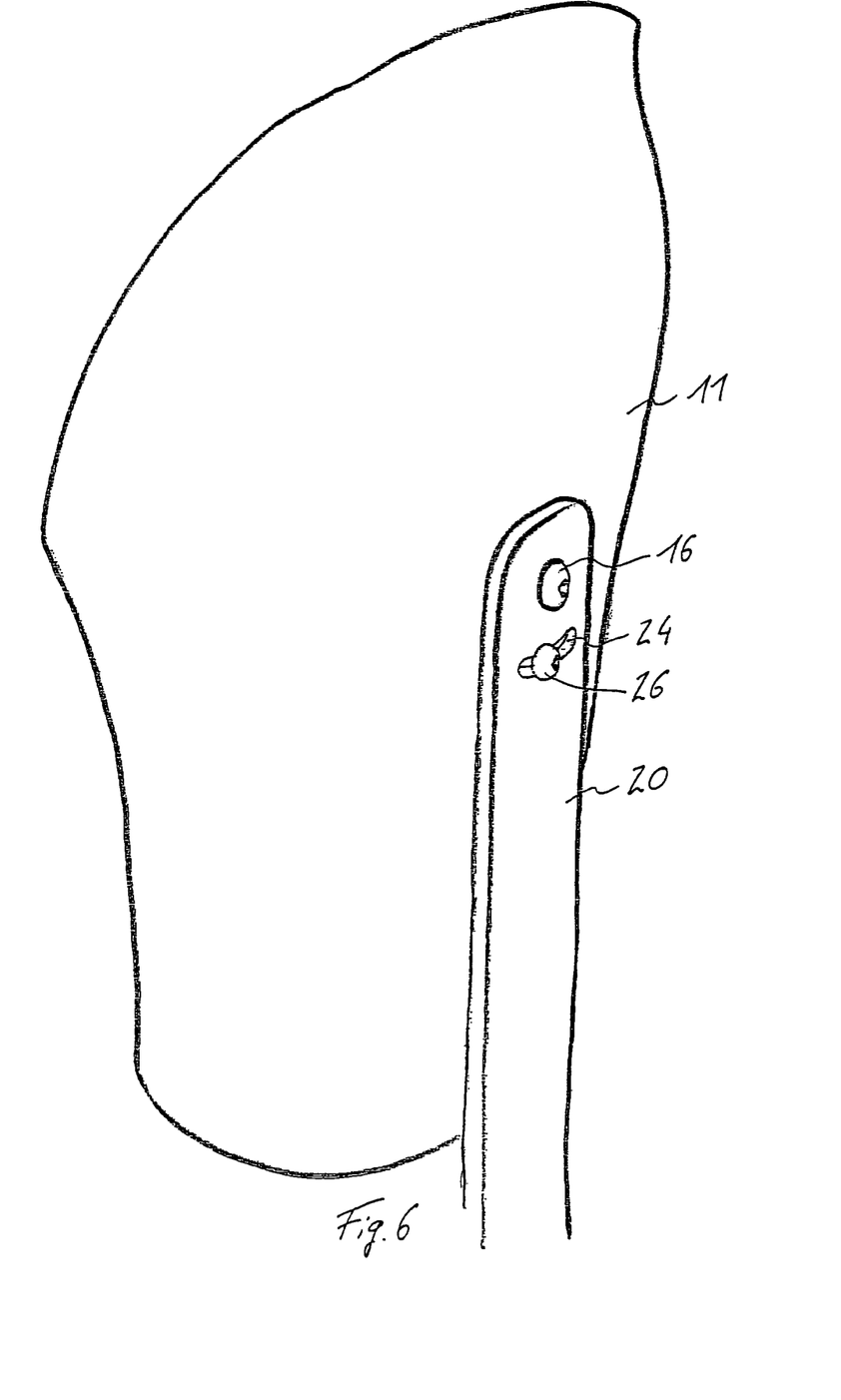
FIG. 6 shows a detail of a partial shell with a fitted frame.

FIG. 6 shows such an embodiment in the assembled state. The lateral partial shell 11 is in this case secured on the frame 20 via a screw-in pin 16 as the connecting means. Another screw 24 is also guided in the curved oblong hole 24 and protrudes through the oblong hole 24 and is screwed into the lateral partial shell 11. Suitable threads can be worked and laminated into the plastic of the partial shell 11 in order to permit stable securing of the frame 20 to the partial shell 11.

Figures 7, 8:
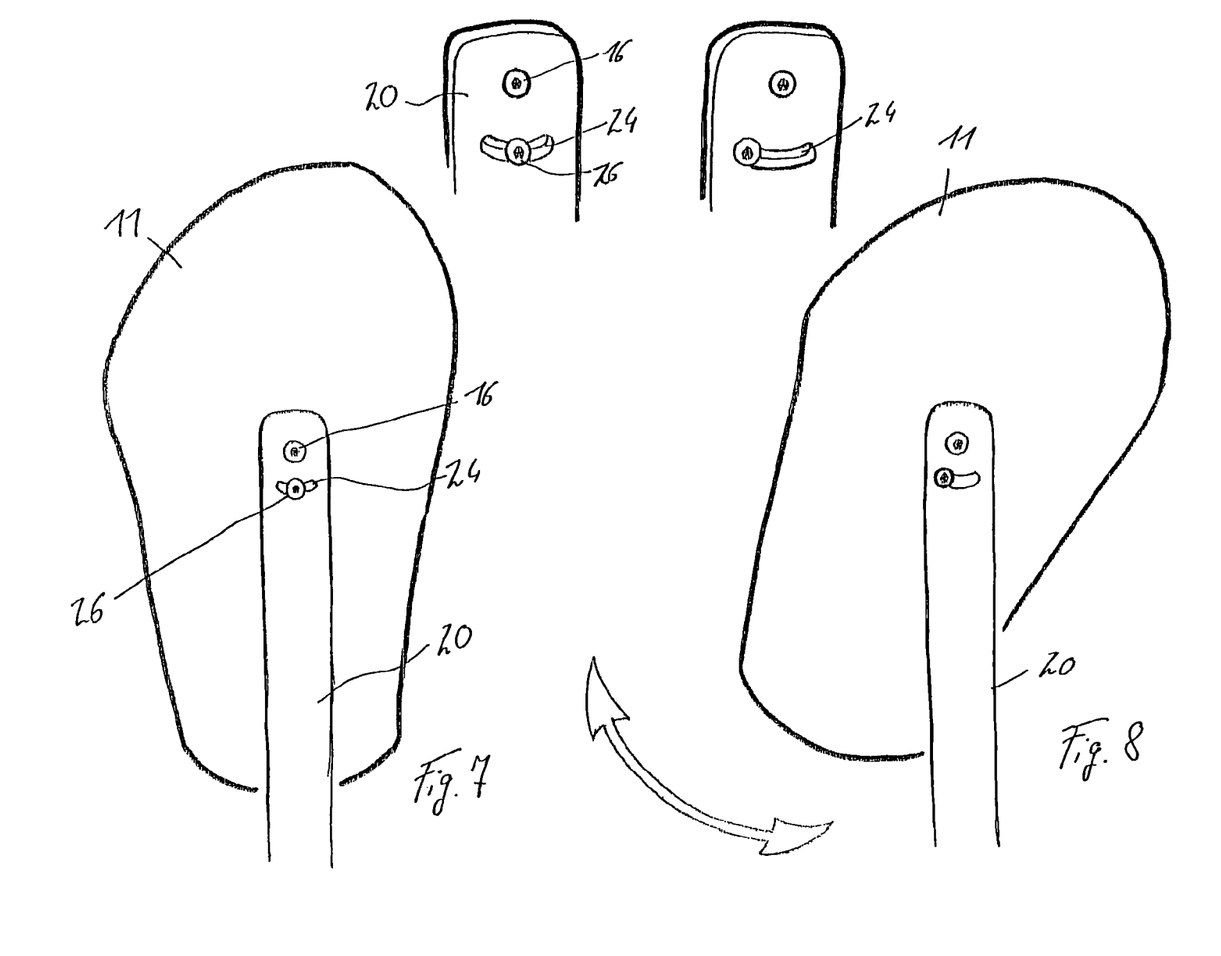
FIG. 7 shows a side view of a fitted partial shell.
FIG. 8 shows a pivoted partial shell.

FIG. 7 shows a side view of the state according to FIG. 6. FIG. 8 shows that the prosthesis socket 1, here the partial shell 11, is pivotable relative to the frame 20 about the connecting means 16 in the form of a screw, this pivoting being indicated by the double arrow. The screw 26 slides to and from inside the oblong hole 24 until an optimal orientation of the prosthesis socket with respect to the frame 20 is found. The screw 26 is then tightened and the thigh socket 1 is fixed relative to the frame 20. This kind of adjustability is necessary since the hip muscles tend to shorten when no extension takes place. When the subject is for the most part in a seated position, the groin muscles contract, and the same is true when a counterweight is absent on account of the amputation. The pivotability and adjustability are advantageous in terms of compensating for this flexion and providing a correct prosthesis setup.

The system of prosthesis socket 1 and prosthesis device 2 makes sitting comfortable, and the prosthesis is also easy to apply and take off. Adaptation to a varying stump volume is easy, and there is no need for lengthy trial fittings or for taking impressions of the patient's stump. The joint device 21, for example, can make sitting down and standing up easier, since various locking modes and damping stages can be set. It is also possible to design the prosthetic joint 21 as a lockable knee joint. In addition to its use in the management of geriatric patients, the system can also be used for rapid primary treatment, such that patients experience a period of immobility that is as short as possible. By virtue of the simple adaptation, it is easy to make adjustments so the stump volume, which adjustments may be reversed on account of the healing process. The adjustment is done by moving the separate partial shells 11, 12 relative to each other, so as to be able to allow for the changing circumferences of the amputation stump.

Figure 9:
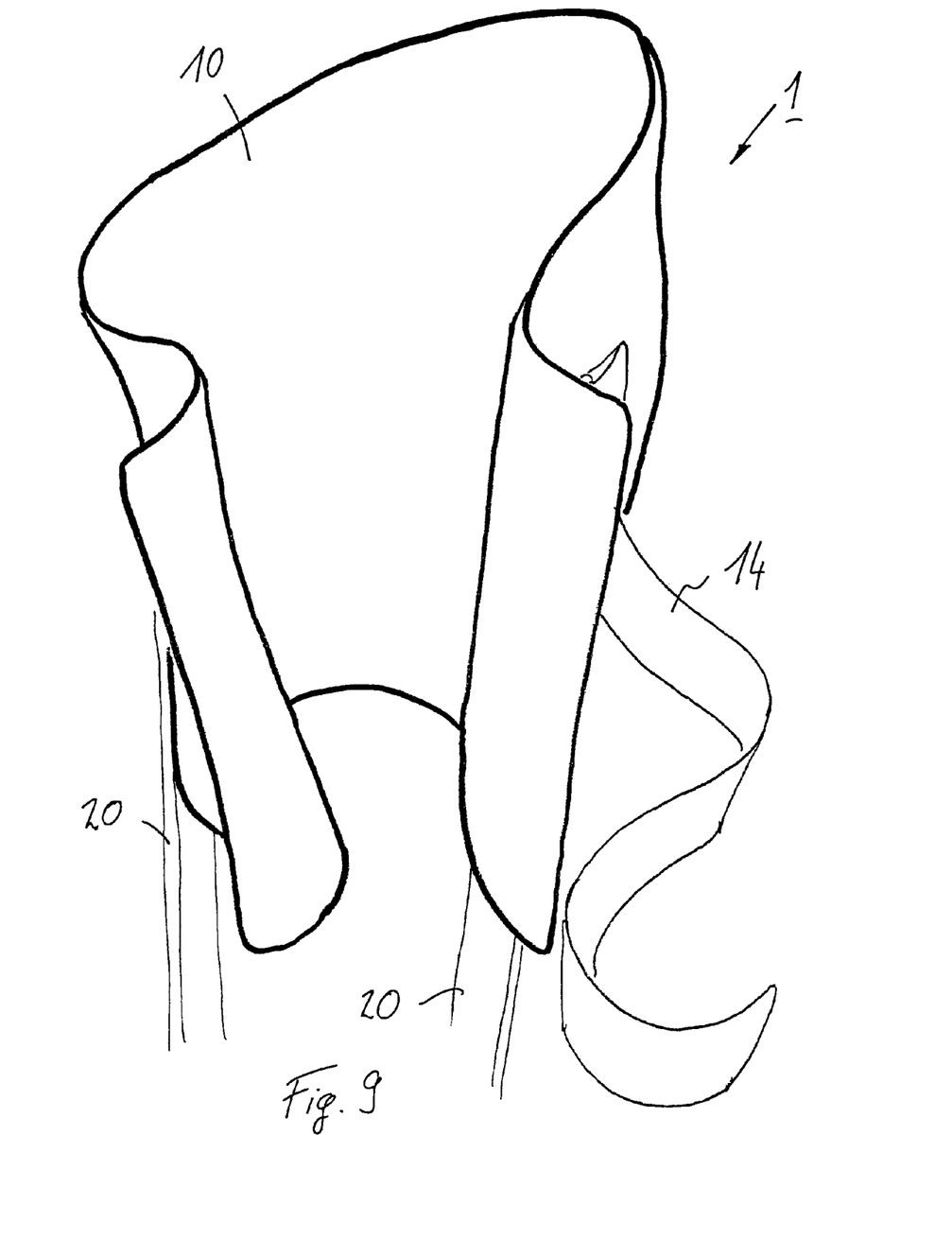
FIG. 9 shows an alternative embodiment of the socket in an open position.

FIG. 9 shows a perspective view of an alternative embodiment of the invention with a one-part shell 10, which has an open cross section and is shown in an opened state. The opening is oriented to the front here, such that the prosthesis socket 1 can be easily applied by opening up the prosthesis socket 10 and placing the stump, provided with a liner, into the opened prosthesis socket or into the opened, shell 10. For this, purpose, the shell ends can be drawn apart from each other and can easily curve outward, so as to permit simple insertion. The shell ends are then placed over each other, with the left-hand shell end in this case being placed under the right-hand, lateral shell end, such that an overlap is obtained at the front. The tensioning means 14 is then guided through a loop, for example, and turned back to permit securing. The securing can be achieved by velcro closures or so-called ski-boot fasteners.

It will be seen from FIG. 9 that the distal end of the shell 10 is open, such that it is easy to adapt, to different stump lengths, without adversely affecting the securing of the shell 10 at the correct site.

Figure 10:
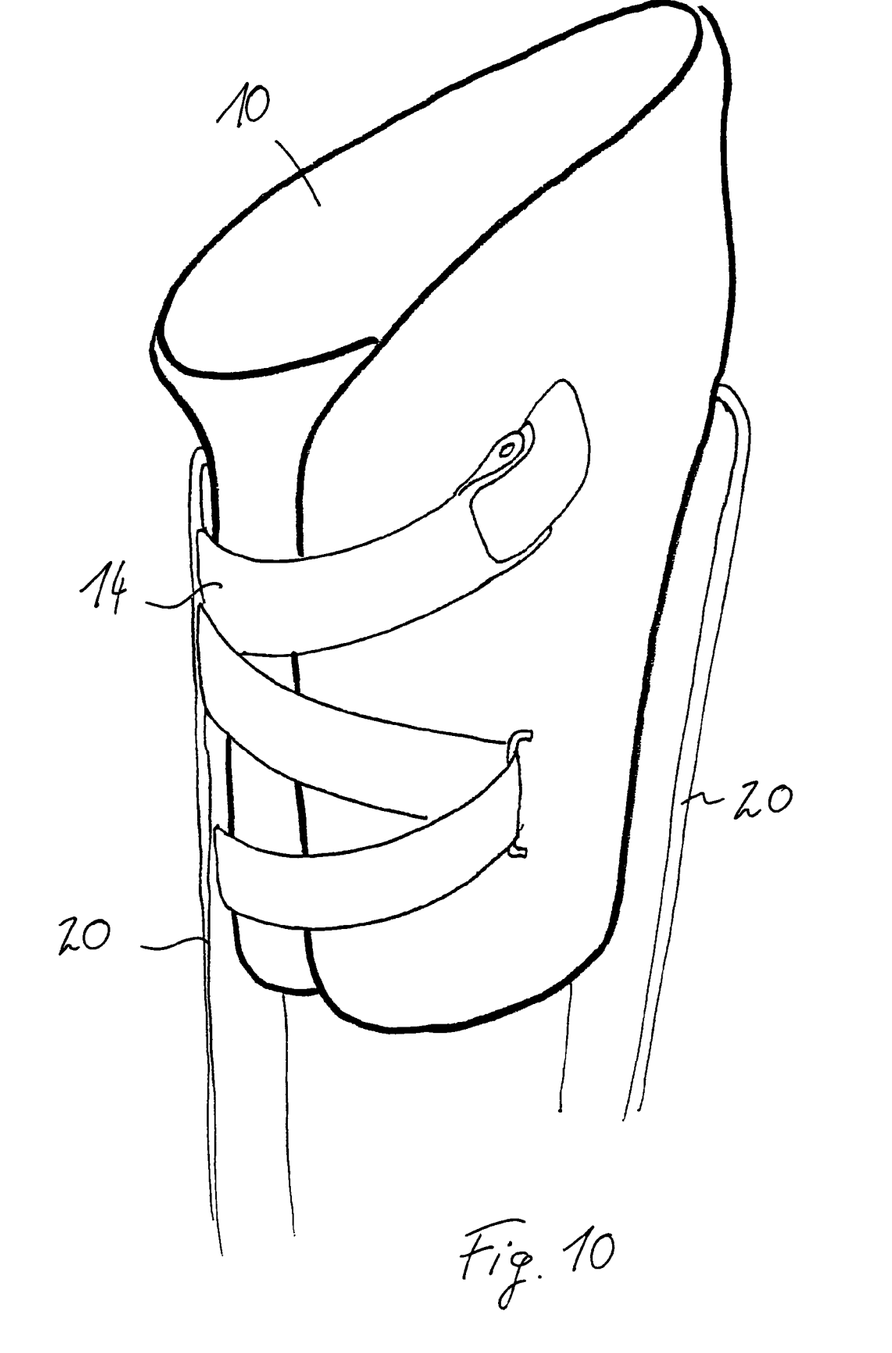
FIG. 10 shows a prosthesis socket according to FIG. 9 in a closed position.

In FIG. 10, the illustrative embodiment according to FIG. 9 is shown in a closed state in which the left-hand shell end is placed underneath the right-hand shell end. The tensioning means 14 is secured in a zigzag formation on the shell 10 of the prosthesis socket and guided in an eyelet at the turning points. The tensioning means 14 can be secured on the outer surface of the shell 10 by velcro closures, or an alternative securing means can also be provided. Tightening can take place via a toggle mechanism arranged at one end or via a ski-boot fastener. It will also be seen from FIG. 10 that the distal end of the prosthesis socket is open, and the end can also foe closed off or delimited by a closure cap. The shell 10 has a spiral-shaped arrangement such that, when the circumference is adjusted, the shell ends slide in a spiral formation around each other or the right-hand end of the shell 10 slides over the inner, left-hand end of the shell.

The invention claimed is:

1. A prosthesis socket for receiving an amputation stump of an extremity, comprising:
    at least one shell which has a curved, open cross section and of which shell ends, in the applied state, at least partially overlap each other;
    at least one tensioning means arranged on the at least one shell, said at least one tensioning means is configured to act in a circumferential direction to tension the shell ends relative to each other; and
    at least one connector associated with said at least one shell for connecting a distal prosthesis device, wherein the at least one connector is configured as a pivotable bearing of the distal prosthesis device relative to said at least one shell and is configured to be arranged in an area which corresponds to a patient's greater trochanter; and
    at least one fixing device for adjustably orienting the distal prosthesis device relative to the at least one shell about a center of rotation of the at least one connector,
    wherein the at least one shell is made from a dimensionally stable plastic with areas of different elasticity with at least a portion of a proximal area of said at least one shell being relatively more flexible than other areas of said of said at least one shell.

2. The prosthesis socket as claimed in claim 1, wherein the at least one shell is comprised of several partial shells.

3. The prosthesis socket as claimed in claim 1, wherein the at least one shell is comprised of at least two shells arranged medially and laterally with respect to an amputation stump.

4. The prosthesis socket as claimed in claim 1, wherein said at least a portion of said proximal area is in a lateral part of said at least one shell.

5. The prosthesis socket as claimed in claim 1, wherein the at least one shell is stiff in medial and lateral directions.

6. The prosthesis socket as claimed in claim 1, wherein the at least one shell is configured with a curvature configured to fit about a longitudinal extent of an amputation stump.

7. The prosthesis socket as claimed in claim 1, wherein the at least one shell is shaped for adaptation to an amputation stump.

8. The prosthesis socket as claimed in claim 1, wherein the at least one connector is arranged in a proximal, relatively stiff area of the at least one shell.

9. The prosthesis socket as claimed in claim 1, wherein said at least one fixing device is guided in an oblong hole.

10. The prosthesis socket as claimed in claim 9, wherein the oblong hole is curved.

11. The prosthesis socket as claimed in claim 1, further comprising a cap secured as a distal closure piece on the at least one shell.

12. The prosthesis socket as claimed in claim 11, wherein the cap is secured releasably on the at least one shell.

13. The prosthesis socket as claimed in claim 1, wherein an inner face of the at least one shell has a direction-dependent surface configuration that provides greater resistance counter to a direction of insertion of an amputation stump than in a direction of insertion of an amputation stump.

14. The prosthesis socket as claimed in claim 13, wherein the surface configuration is a nap velour oriented in a distal direction of said at least one shell.

15. The prosthesis socket as claimed in claim 1 wherein one or more inner faces of said at least one shell are coated with an adhesive layer.

16. The prosthesis socket as claimed in claim 1, wherein the at least one tensioning means is selected from the group consisting of velcro tapes, ski-boot fasteners, clips, and straps.

17. The prosthesis socket as claimed in claim 1, wherein the at least one tensioning means are positioned on a front portion of said at least one shell.

18. The prosthesis socket as claimed in claim 1, wherein the at least one tensioning means includes two tensioning means that are axially offset on the at least one shell.

19. The prosthesis socket as claimed in claim 1, wherein the at least one tensioning means are configured to act in a circular configuration.

20. The prosthesis socket as claimed in claim 1, wherein the at least one tensioning means is arranged on the at least one shell with two axially offset guides.

21. The prosthesis socket as claimed in claim 1, wherein the at least one shell forms a cone that widens in a proximal direction.

22. The prosthesis socket as claimed in claim 1, further comprising a frame secured one of laterally or medially to said at least one connector.

23. The prosthesis socket as claimed in claim 22, wherein the frame is configured as an outer frame.

24. The prosthesis socket as claimed in claim 22, wherein the frame is produced from a metal profile.

25. The prosthesis socket as claimed in claim 22, further comprising a joint device secured on the frame.

26. A system comprising:
a prosthesis socket for receiving an amputation stump of an extremity, including
at least one shell which has a curved, open cross section and of which shell ends, in the applied state, at least partially overlap each other;
at least one tensioning means arranged on the at least one shell, said at least one tensioning means is configured to act in a circumferential direction to tension the shell ends relative to each other; and
at least one connector associated with said at least one shell for connecting a distal prosthesis device, wherein the at least one connector is configured as a pivotable bearing of the distal prosthesis device relative to said at least one shell and is configured to be arranged in an area which corresponds to a patient's greater trochanter; and
at least one fixing device for adjustably orienting the distal prosthesis device relative to the at least one shell about a center of rotation of the at least one connector,
wherein the at least one shell is made from a dimensionally stable plastic with areas of different elasticity with at least a portion of a proximal area of said at least one shell being relatively more flexible than other areas of said of said at least one shell; and
a prosthesis device secured to said at least one connector.

27. A prosthesis socket for receiving an amputation stump of an extremity, comprising:
at least one shell which has a curved, open cross section and of which shell ends, in the applied state, at least partially overlap each other;
at least one tensioning means arranged on the at least one shell, said at least one tensioning means is configured to act in a circumferential direction to tension the shell ends relative to each other; and
at least one connector associated with said at least one shell for connecting a distal prosthesis device, wherein the at least one connector is configured as a pivotable bearing of the distal prosthesis device relative to said at least one shell and is configured to be arranged in an area which corresponds to a patient's greater trochanter; and
at least one fixing device for adjustably orienting the distal prosthesis device relative to the at least one shell about a center of rotation of the at least one connector,
wherein the at least one shell is made from a dimensionally stable plastic with areas of different elasticity.

28. A prosthesis socket for receiving an amputation stump of an extremity, comprising:
at least one shell which has a curved, open cross section and of which shell ends, in the applied state, at least partially overlap each other;
at least one tensioning means arranged on the at least one shell, said at least one tensioning means is configured to act in a circumferential direction to tension the shell ends relative to each other;
at least one connector associated with said at least one shell for connecting a distal prosthesis device,
wherein the at least one shell is made from a dimensionally stable plastic with areas of different elasticity, and
wherein the at least one connector is configured for pivotable bearing of the distal prosthesis device and configured in an area which corresponds to a patient's greater trochanter; and
one or more fixing devices for orienting the distal prosthesis device relative to the at least one shell.

29. A prosthesis socket for receiving an amputation stump of an extremity, comprising:
at least one shell which has a curved, open cross section and of which shell ends, in the applied state, at least partially overlap each other;
at least one tensioning means arranged on the at least one shell, said at least one tensioning means is configured to act in a circumferential direction to tension the shell ends relative to each other; and
at least one connector associated with said at least one shell for connecting a distal prosthesis device, wherein the at least one connector is configured as a pivotable bearing of the distal prosthesis device relative to said at least one shell and is configured to be arranged in an area which corresponds to a patient's greater trochanter; and
at least one fixing device for adjustably orienting the distal prosthesis device relative to the at least one shell about a center of rotation of the at least one connector,
wherein the at least one shell is made from a dimensionally stable plastic with areas of different elasticity, and
wherein an inner face of the at least one shell has a direction-dependent surface configuration that provides greater resistance counter to a direction of insertion of an amputation stump than in a direction of insertion of an amputation stump.

* * * * *